United States Patent
Miladinov et al.

(12)

(10) Patent No.: US 7,025,996 B1
(45) Date of Patent: Apr. 11, 2006

(54) DIETARY SUPPLEMENT FOR MEDICAL PATIENTS

(76) Inventors: Vesselin Danailov Miladinov, 5224 Emmeryville La., Keller, TX (US) 76248; Riccardo Domenico Roscetti, 2221 Cypress Island Dr., Apt. 204, Pompano Beach, FL (US) 33069

( * ) Notice: Subject to any disclaimer, the term of this patent is extended or adjusted under 35 U.S.C. 154(b) by 278 days.

(21) Appl. No.: 10/690,234

(22) Filed: Oct. 21, 2003

(51) Int. Cl.
*A61K 35/78* (2006.01)

(52) U.S. Cl. ..................................... 424/725
(58) Field of Classification Search ............... 424/725
See application file for complete search history.

*Primary Examiner*—Michael Meller
(74) *Attorney, Agent, or Firm*—Gold & Rizvi, P.A.; H. John Rizvi; Glenn E. Gold

(57) ABSTRACT

A dietary supplement which is formulated for medical patients, particularly cancer patients undergoing a chemotherapy treatment regimen. The ingredients are formulated in a form which is easiest for the patient to digest, with consideration of the damage that chemotherapy causes to the digestive system. The dietary supplement provides an ample and well-balanced source of essential and non-essential amino acids, as well as vitamins and minerals. The amino acids are preferably provided in the form of free amino acids, which can be directly absorbed into the bloodstream without digestion. The supplement is formulated in such a manner that it can be used as the sole nutritional source for substantial periods of time.

12 Claims, 1 Drawing Sheet

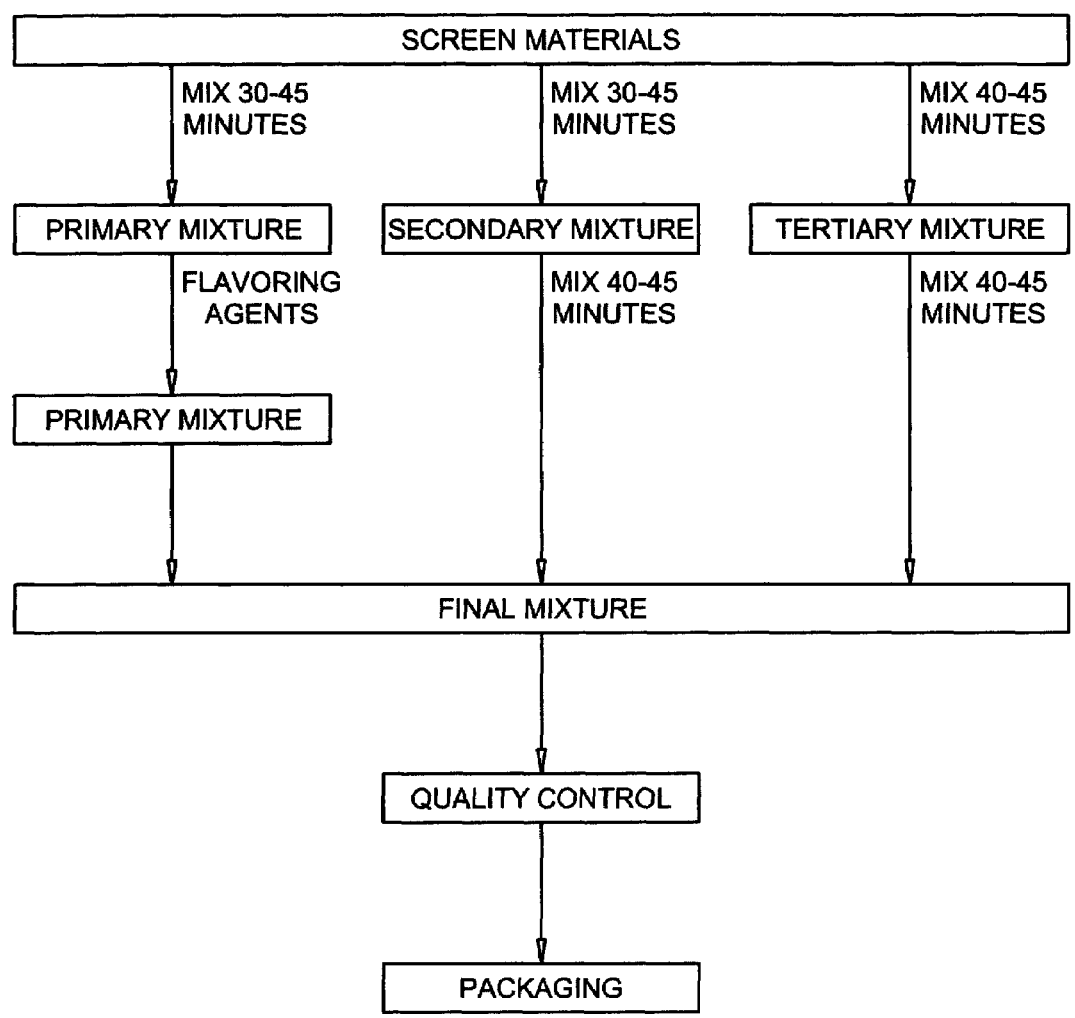

DIETARY SUPPLEMENT FOR MEDICAL PATIENTS

BACKGROUND OF THE INVENTION

1. Field of the Invention

The present invention generally relates to dietary supplements for medical patients, and more particularly, to a dietary supplement which is formulated to meet the specific nutrient demands of chemotherapy patients. The dietary supplement includes a palatable composition containing sugars, lipids and amino acids, as well as vitamins and minerals, and can be used as a sole nutrition source for extended periods of time.

2. Description of the Prior Art

Patients diagnosed with cancer usually undergo a treatment plan for curing or managing progression or symptoms of the disease. These treatment plans commonly include surgery, radiation therapy, chemotherapy, hormone therapy, immunotherapy or some combination of these therapies. While the aim of these therapies is to kill cancer cells, some healthy cells also become damaged and killed in the treatment process. The death of healthy cells causes various side effects in cancer patients, such as loss of appetite, weight loss or gain, sore mouth or throat, nausea, and vomiting. These side effects can significantly hinder the cancer patient's ability to eat and assimilate necessary nutrients.

Persons who are healthy generally find it easy to consume the types and quantities of foods required for overall good health. General nutrition guidelines typically stress consumption of large quantities of fruits, vegetables and whole-grain products; moderate quantities of low-fat meat and dairy foods; and low quantities of fat, sugar, alcohol and salt, for optimum health. Patients undergoing chemotherapy treatment, however, may find healthy eating a challenge, due to the many potential adverse side effects of the chemotherapy regimen. For example, the chemotherapy regimen has a tendency to damage the digestive system of the cancer patient, and thus, the supplement or diet must be taken in a form that is easy for the patient to digest. Cancer and cancer treatments may also alter the body's ability to tolerate certain foods and to use nutrients. Consequently, the diet of the cancer patient usually requires significant adjustments in order to enable the patient to withstand the ravages of the disease and the stresses and effects of treatment.

Nutrition programs for cancer patients typically emphasize the consumption of high-calorie, high-protein foods such as milk, cheese and cooked eggs. In the event that the patient suffers excessive weight loss, the patient may be advised to increase consumption of sauces and gravies and to include more butter, margarine, or oil in the patient's diet to increase calorie consumption. The patient may be advised to decrease consumption of high-fiber foods, since these have a tendency to aggravate digestive conditions such as diarrhea.

Adopting a balanced and appropriate nutrition program enables cancer patients to feel better, maintain strength and energy, maintain body weight and store of nutrients, tolerate treatment-related side effects, decrease risk of infection by strengthening the immune system, and expedite healing and recovery. Nutrients that are regarded as essential ingredients of a cancer patient's diet include protein, carbohydrates, fats, vitamins and minerals. Protein helps to ensure growth, repair body tissue, and maintain a healthy immune system. Carbohydrates and fats are needed to supply the body with the bulk of the calories it needs. Vitamins and minerals help ensure proper growth and development and enable the body to use as energy the calories supplied in foods.

A variety of food supplements and diets specifically formulated for athletes, the elderly, pregnant women and other specific groups are known in the art. However, these supplements or diets are generally not suitable for persons afflicted with disease such as HIV, AIDS, short bowel syndrome, Crohn's disease or cancer patients undergoing chemotherapy treatment. Certain common nutrients such as calcium must be excluded from the supplement or diet, since cancer patients tend to accumulate excessively high levels of calcium or the other nutrients. Calcium intolerance associated with chemotherapy precludes patients' use of common commercially available calcium-containing dietary supplements that may otherwise contain the ingredients necessary for proper nutrition of the patient.

Digestive enzymes of the small intestine are embedded within the cell membrane of the microvilli. These enzymes are responsible for the breakdown of large proteins to their basic free amino acid. The enzymes are not secreted in the lumen but remain attached to the cell membrane, with the active site of the enzyme exposed to the chyme. One such brush border enzyme is enterokinase, which is required for the activation of the protein-digesting enzyme, trypsin. Trypsin, which cleaves internal peptide bonds, is also an activator for other enzymes that cause the further digestion of proteins, to the digestion of fatty acids from phospholipids, such as lecithin. Therefore, the intestinal surface area is directly related to the process of digestion. The reduction in epithelial surface area in the small intestines caused by chemotherapy greatly reduces digestion and absorption. This requires nutritional supplements for cancer patients to be easily digestible.

In the digestion of proteins, tripeptides are digested to dipeptides, and the dipeptides are digested to free amino acids. The free amino acids are absorbed into epithelial cells and secreted into the blood. Tripeptides and dipeptides may enter the epithelial cell via other transport carriers, but are further digested to amino acids before they are secreted into the blood. Accordingly, proteins are most easily digested when amino acids are ingested in the free form, preventing the need for further digesting tripeptides and dipeptides into the individual amino acids.

Vitamins are organic molecules that are needed in small amounts in the diet. Humans do not have the capacity to synthesize vitamins, and vitamins must therefore be obtained in the diet. Vitamin A is essential for good vision and healthy skin, hair and mucous membranes of the nose, throat, respiratory system and digestive system. Since the mucous membranes are highly affected by chemotherapy treatment, vitamin A supplementation is of utmost importance to the cancer patient. Vitamin A also stimulates the healing of wounds and is used to treat skin disorders. Beta-carotene, which accumulates in human skin, is a precursor of vitamin A. Excess beta-carotene, along with other carotenoids, acts as an antioxidant and supports immune function to enhance the body's resistance to infections. Vitamin A may help prevent some cancers and vision problems. While vitamin A may be toxic when stored in the body for extended periods of time, beta-carotene is not toxic, even in high doses.

Thiamine, or vitamin B1, is associated with carbohydrate, fat, and protein metabolism. It helps to convert excess glucose into fat and participates in nerve impulse transmission and maintains normal appetite, muscle tone, and mental health. Mild vitamin B1 deficiencies cause fatigue, loss of appetite, nausea, moodiness, confusion, and anemia. Vitamin B5, or pantothenic acid, is required for converting food into energy, building red blood cells, making bile and synthesizing fats, steroids, antibodies and neurotransmitters. Pantothenic acid in lotions and creams reduces the pain of burns, cuts and abrasions, reduces skin inflammation, and speeds wound healing. Vitamin B6 (pyridoxine, pyridoxamine, and pyridoxal) supports the immune system, nerve impulse transmission, energy metabolism, and red blood cell synthesis. Excessive or inadequate levels of vitamin B6 can impair nerve function and mental health. Vitamin B12 (cobalamin), like the other B vitamins, is important for converting fats, carbohydrates, and protein into energy and assisting in the synthesis of red blood cells.

Vitamin C, or ascorbic acid, is known for its ability to prevent and treat scurvy. Connective tissue throughout the body is made of collagen, which depends on vitamin C for its production. In this role, vitamin C helps heal wounds, burns, bruises, and broken bones. As a powerful antioxidant and immune system buster, vitamin C may alleviate the pain of rheumatoid arthritis, protect against arteriosclerosis and heart disease, and help prevent some forms of cancer. Since it is water-soluble, excess vitamin C is excreted in the urine, so large quantities of it may usually be taken without fear of toxicity.

Vitamin D, or cholecalciferol, promotes healthy bones and teeth by regulating the absorption and balance of calcium and phosphorus and fosters normal muscle contraction and nerve function. Supplements of vitamin D may help treat psoriasis and slow or even reverse some cancers such as myeloid leukemia. Vitamin D is fat-soluble; thus, excessive quantities of vitamin D are stored in the body. Because of its potentially toxic effects, vitamin D should not be taken in supplements of more than 400 IU daily unless prescribed by a doctor. The quantities in the current formula of the present invention are reduced to 200 IU (a sum of the recommended five servings a day).

Vitamin E encompasses a family of compounds called tocopherols, of which the alpha tocopherol is the most common. It is required for proper functioning of the immune system, endocrine system, and sex glands. As a powerful antioxidant, vitamin E prevents free radicals from damaging cells and tissues. In this capacity, vitamin E deters atheroscherosis, accelerates the healing of the wounds, protects lung tissue from inhaled pollutants, may reduce risk of heart disease, and may prevent premature skin aging. It is suspected that vitamin E can prevent cancer. Although it is fat soluble, vitamin E is considered nontoxic because it does not cause toxic effects unless administered at very high doses.

Vitamin K (menadione, phytonadione), is required in small but critical quantities to form essential proteins, mainly for blood clotting, but also for kidney function and bone metabolism. Vitamin K exists in two natural forms that require some dietary fat for absorption. Vitamin K is synthesized by intestinal bacteria and released into the intestines for absorption into the bloodstream.

There is an established need for a dietary supplement which is readily available, includes free amino acids for easy digestion, includes vitamins and minerals formulated to meet the nutritional needs of patients undergoing cancer treatment, and which can be used as a sole nutritional source for extended periods of time.

SUMMARY OF THE INVENTION

The present invention is directed to a dietary supplement which contains most or all of the nutrients necessary for imparting strength, energy, tissue healing and repair, growth and development, and treatment tolerance to a cancer patient undergoing a cancer treatment regimen, in a form which is readily available, easily digestible and nutritionally complete.

An object of the present invention is to provide a dietary supplement that is specifically formulated to meet the nutritional needs of cancer patients undergoing cancer treatment.

Another object of the present invention is to provide a dietary supplement that may be used as a sole source of nutrition for a cancer patient over an extended period of time.

Still another object of the present invention is to provide a dietary supplement that is provided in an easily digestible form for utilization by cancer patients.

Yet another object of the present invention is to provide a dietary supplement that contains a complete or nearly complete supply of essential nutrients to cancer patients.

A still further object of the present invention is to provide a dietary supplement that constitutes an ample and well-balanced source of essential and non-essential amino acids, as well as other nutrients such as sugars and fats or lipids.

These and other objects, features and advantages of the present invention will become more readily apparent from the attached drawings and the detailed description of the preferred embodiments, which follow.

BRIEF DESCRIPTION OF THE DRAWINGS

The invention will be further understood, by way of example, with reference to the accompanying drawing, in which:

FIG. 1 is a flow diagram illustrating a typical method for synthesizing the dietary supplement of the present invention.

DETAILED DESCRIPTION OF THE PREFERRED EMBODIMENTS

The present invention comprises a nutrient supplement that is formulated to meet the needs of cancer patients, particularly cancer patients undergoing a chemotherapy treatment regimen. In addition to meeting the specific needs of chemotherapy patients, the dietary supplement of the present invention provides a complete or nearly complete supply of nutrients essential for chemotherapy patients. The ingredients are formulated in a form that is easiest for the patient to digest, with consideration of the damage that chemotherapy causes to the digestive system. The dietary supplement provides an ample and well-balanced source of essential and non-essential amino acids. The amino acids are preferably provided in the form of free amino acids, which can be directly absorbed into the bloodstream without digestion. The supplement is formulated in such a manner that it can be used as the sole nutritional source for substantial period of time. Therefore, certain vitamins and minerals that may be physiologically unfavorable in quantities that exceed the recommended daily values may be either provided in smaller quantities or omitted.

In a preferred embodiment, the dietary supplement of the present invention includes selected quantities of the following components: fructose, maltodextrin, dextrose, sugar, hydrolyzed whey protein, flaxseed oil, corn oil, sunflower oil, soybean oil, margarine, isoleucine, leucine, lysine, methionine, phenylalanine, threonine, valine, histidine, glutamine, lecithin, ascorbic acid, niacin, alpha tocopheryl acetate, pantothenic acid, pyridoxine hydrochloride, riboflavin, thiamine mononitrate, beta carotene, folic acid, biotin, phtonadione, cyanocabalamin, microcrystalline cellulose, magnesium gluconate, zinc sulfate heptahydrate, ferrous sulfate heptahydrate, and potassium citrate monohydrate.

In a preferred embodiment, a daily serving or dosage of the dietary supplement of the present invention includes about 5–60 g of fructose, about 2–30 g of maltodextrin, about 1–15 g of dextrose, about 1–60 g of sugar, about 15–90 g of hydrolyzed whey protein, about 0.5–6 g of flaxseed oil, about 0.5–6 g of corn oil, about 0.5–6 g of sunflower oil, about 0.5–6 g of soybean oil, about 0.5–6 g of margarine, about 0.2–1.5 g of isoleucine, about 0.5–2.0 g of leucine, about 0.5–2 g of lysine, about 0.5–2 g of methionine, about 0.5–2 g of phenylalanine, about 0.2–1 g of threonine, about 0.4–1.5 g of valine, about 0.4–1.5 g of histidine, about 1–30 g of glutamine, about 1–8 g of lecithin, about 0.01–0.02 g of ascorbic acid, about 0.005—about 0.030 g of niacin, about 5–30 IU (International Units) of alpha tocopheryl acetate, about 0.002–0.010 g of pantothenic acid, about 0.005—about 0.020 g of pyridoxine hydrochloride, about 0.005—about 0.020 g of riboflavin, about 0.005—about 0.020 g of thiamine mononitrate, about 500—about 2,000 IU of beta carotene, about 0.0001—about 0.0005 g of folic acid, about 0.00002–0.0004 g of biotin, about 0.00002—about 0.00004 g of phtonadione, about 0.000001–0.000002 g of cyanocabalamin, about 1–10 g of microcrystalline cellulose, about 0.1–0.4 g of magnesium gluconate, about 0.03–0.08 g of zinc sulfate heptahydrate, about 0.03–0.1 g of ferrous sulfate heptahydrate, and about 1–5 g of potassium citrate monohydrate.

In a most preferred embodiment, the dietary supplement of the present invention includes selected quantities of the following components: whey protein, glutamine, fructose, maltrin, oat bran, flaxseed oil powder, margarine powder, isoleucine, leucine, lysine, methionine, phenylalanine, threonine, valine, histidine, ascorbic acid, niacin, vitamin E, pantothenic acid, vitamin B6, riboflavin, thiamine monocitrate, beta carotene, folic acid, biotin, vitamin K, cyanocoalbumin, vitamin D3, magnesium gluconate, zinc sulfate heptahydrate, iron sulfate heptahydrate and potassium citrate monohydrate. Flavor agents such as vanilla extract liquid, French vanilla S.D. flavor, lecithin and dextrose may be included in the supplement. Alternative flavoring agents known by those skilled in the art may be used in addition to or instead of those listed above.

In a most preferred embodiment, a daily serving or dosage of the dietary supplement of the present invention includes about 15,000 mg—about 90,000 mg, and preferably, about 45,000 mg of whey protein; about 1,000 mg—about 30,000 mg, and preferably, about 15,000 mg of glutamine; about 5,000 mg—about 60,000 mg, and preferably, about 35,000 mg of fructose; about 2,000 mg—about 30,000 mg, and preferably, about 15,000 mg of maltrin; about 1,500 mg—about 90,000 mg, and preferably, about 5000 mg oat bran; about 500 mg—about 6000 mg, and preferably, about 2,500 mg, of flaxseed oil powder; about 500 mg—about 6,000 mg, and preferably, 1,500 mg of margarine powder; about 200 mg–1500 mg, and preferably, 750 mg of isoleucine; about 500 mg—about 2,000 mg, and preferably, about 1,050 mg, leucine; about 500 mg—about 2,000 mg, and preferably, about 900 mg of lysine; about 500 mg—about 2,000 mg, and preferably, about 980 mg of methionine; about 500 mg—about 2,000 mg, and preferably, about 1050 mg of phenylalanine; about 200 mg—about 1,000 mg, and preferably, about 530 mg of threonine; about 400 mg—about 1,500 mg, and preferably, about 750 mg of valine; about 400 mg—about 1,500 mg, and preferably, 750 mg of histidine; about 10 mg—about 200 mg, and preferably, about 80 mg, of ascorbic acid; about 5 mg—about 30 mg, and preferably, about 15 mg of niacin; about 630 IU (International Units), or about 0.03 mg, of vitamin E; about 2 mg—about 10 mg, and preferably, about 7 mg of pantothenic acid; about 0.5 mg—about 2.0 mg, and preferably, about 1.60 mg of vitamin B6; about 0.5 mg—about 2.0 mg, and preferably, about 1.60 mg of riboflavin; about 0.5 mg—about 2.0 mg, and preferably, about 1.20 mg of thiamine monocitrate; about 2.99 mg of beta carotene; about 0.1 mg—about 0.5 mg, and preferably, about 0.33 mg of folic acid (10%); about 2.0 mg—about 4.0 mg, and preferably, about 3.0 mg of biotin 1% DCP; about 0.2 mg—about 1.0 mg, and preferably, about 0.60 mg of vitamin K 5%; about 0.1 mg—about 0.2 mg, and preferably, about 0.2 mg of cyanocoalbumin 1%; about 1.00 mg of vitamin D3; about 100 mg—about 400 mg, and preferably, about 300 mg of magnesium gluconate; about 30 mg—about 80 mg, and preferably, about 60 mg of zinc sulfate heptahydrate; about 30 mg—about 100 mg, and preferably about 70 mg of iron sulfate heptahydrate; and about 1,000 mg—about 5,000 mg, and preferably about 3,000 mg of potassium citrate monohydrate. About 10,000 mg of vanilla extract liquid, about 10 mg of French Vanilla S.D. flavor, about 3750 mg of lecithin, and about 7,500 mg of dextrose may be included in the supplement.

Referring to the flow diagram of FIG. 1, a batch of the dietary supplement of the present invention is typically prepared as follows. First, each of the components is weighed in the appropriate proportions for the batch size and stored in separate containers. Each of the containers is preferably marked with the name of the component, the weight of the component and the batch number. After all of the components have been sifted through a mesh screen, the whey protein, glutamine and vanilla extract liquid are thoroughly mixed for typically about 30–45 minutes to form a primary homogenous mixture. The fructose, maltrin, oat bran, flaxseed oil powder, margarine powder, isoleucine, leucine, lysine, methionine, phenylalanine, threonine, valine and histidine are then thoroughly for typically about 40–45 minutes to form a secondary homogenous mixture. The ascorbic acid, niacin, vitamin E, pantothenic acid, vitamin B6, riboflavin, thiamine monocitrate, beta carotene, folic acid, biotin, vitamin K, cyanocoalbumin, vitamin D3, magnesium gluconate, zinc sulphate heptahydrate, iron sulfate heptahydrate and potassium citrate monohydrate are then thoroughly mixed for typically about 40–45 minutes to form a tertiary homogenous mixture. The French vanilla S.D. flavor, lecithin and dextrose flavoring agents are then added to and thoroughly mixed with the primary homogenous mixture. Finally, the primary, secondary and tertiary mixtures are added and thoroughly mixed together for typically about 40–45 minutes to define a homogenous final mixture which defines the finished dietary supplement product. After quality control procedures are carried out, the final mixture is packaged.

The invention will be better understood by reference to the accompanying examples.

EXAMPLE 1

Weighing and Labeling

The multiple components corresponding to a one-day dose of the dietary supplement of the present invention were prepared for mixing by initially weighing the components and placing the components in 36 (thirty-six) separate labeled containers in the following quantities: 45,000 mg of whey protein; 15,000 mg of glutamine; 35,000 mg of fructose; 15,000 mg of maltrin; 5,000 mg of oat bran; 2,500 mg of flaxseed oil powder; 1,500 mg of margarine powder; 750 mg of isoleucine; 1,050 mg of leucine; 900 mg of lysine; 980 mg of methionine; 1050 mg of phenylalanine; 530 mg of threonine; 750 mg of valine; 750 mg of histidine; 80 mg of ascorbic acid; 15 mg of niacin; 0.03 mg of vitamin E; 7 mg of pantothenic acid; 1.60 mg of vitamin B6; 1.60 mg of riboflavin; 1.20 mg of thiamine monocitrate; 2.99 mg of beta carotene; 0.33 mg of folic acid (10%); 3.0 mg of biotin 1%; 0.60 mg of vitamin K 5%; 0.2 mg of cyanocoalbumin 1%; 1.00 mg of vitamin D3; 300 mg of magnesium gluconate; 60 mg of zinc sulfate heptahydrate; 70 mg of iron sulfate heptahydrate; 3,000 mg of potassium citrate monohydrate; 10,000 mg of vanilla extract liquid; 10 mg of French vanilla S.D. flavor; 3,750 mg of lecithin; and 7,500 mg of dextrose.

EXAMPLE 2

Mixing and Preparation

After all of the components in Example 1 were sifted through a mesh screen, the whey protein, glutamine and vanilla extract liquid were blended in a round blender for 45 minutes to form a primary homogenous mixture. The fructose, maltrin, oat bran, flaxseed oil powder, margarine powder, isoleucine, leucine, lysine, methionine, phenylalanine, threonine, valine and histidine were then blended in a drum roller blender for about 40–45 minutes to form a secondary homogenous mixture. The ascorbic acid, niacin, vitamin E, pantothenic acid, vitamin B6, riboflavin, thiamine monocitrate, beta carotene, folic acid, biotin, vitamin K, cyanocoalbumin, vitamin D3, magnesium gluconate, zinc sulphate heptahydrate, iron sulfate heptahydrate and potassium citrate monohydrate were next blended in a drum roller blender for 45 minutes to form a tertiary homogenous mixture. The French Vanilla S.D. Flavor, lecithin and dextrose were then added to the primary homogenous mixture and blended to form a homogenous mixture. Finally, the primary, secondary and tertiary mixtures were added together and mixed in a V-blender for 45 minutes to define a homogenous final mixture that defined the finished dietary supplement product. The dietary supplement composition was subjected to quality control procedures and packaged.

While the preferred embodiments of the invention have been described above, it will be recognized and understood that various modifications can be made in the invention and the appended claims are intended to cover all such modifications which may fall within the spirit and scope of the invention.

What is claimed is:

1. A dietary supplement comprising a homogenous mixture of whey protein, glutamine, fructose, maltrin, oat bran, flaxseed oil powder, margarine powder, isoleucine, leucine, lysine, methionine, phenylalanine, threonine, valine, histidine, ascorbic acid, niacin, vitamin E, pantothenic acid, vitamin B6, riboflavin, thiamine monocitrate, beta carotene, folic acid, biotin, vitamin K, cyanocoalbumin, vitamin D3, magnesium gluconate, zinc sulfate heptahydrate, iron sulfate heptahydrate and potassium citrate monohydrate.

2. The dietary supplement of claim 1 further comprising at least one flavoring agent in said mixture.

3. The dietary supplement of claim 2 wherein said at least one flavoring agent comprises at least one of vanilla extract liquid, French vanilla flavor, lecithin and dextrose.

4. The dietary supplement of claim 3 wherein said at least one flavoring agent comprises about 10,000 mg of said vanilla extract liquid, about 10.00 mg of said French vanilla flavor, about 3,750 mg of said lecithin, and about 7,500 mg of said dextrose.

5. The dietary supplement of claim 1 wherein a daily dose of said mixture comprises about 15,000 mg to about 90,000 mg of said whey protein, about 1,000 mg to about 30,000 mg of said glutamine, about 5,000 mg to about 60,000 mg of said fructose, about 2,000 mg to about 30,000 mg of said maltrin, about 1,500 mg to about 90,000 mg of said oat bran, about 500 mg to about 6,000 mg of said flaxseed oil powder, about 500 mg to about 6,000 mg of said margarine powder, about 200 mg to about 1,500 mg of said isoleucine, about 500 mg to about 2,000 mg of said leucine, about 500 mg to about 2,000 mg of said lysine, about 500 mg to about 2,000 mg of said methionine, about 500 mg to about 2,000 mg of said phenylalanine, about 200 mg to about 1,000 mg of said threonine, about 400 mg to about 1,500 mg of said valine, about 400 mg to about 1,500 mg of said histidine, about 10 mg to about 200 mg of said ascorbic acid, about 5 mg to about 30 mg of said niacin, about 0.03 mg of said vitamin E, about 2 mg to about 10 mg of said pantothenic acid, about 0.5 mg to about 2.00 mg of said vitamin B6, about 0.5 mg to about 2.0 mg of said riboflavin, about 0.5 mg to about 2.0 mg of said thiamine monocitrate, about 2.99 mg of said beta carotene, about 0.1 mg to about 0.5 mg of said folic acid, about 2.0 mg to about 4.0 mg of said biotin, about 0.2 mg to about 1.0 mg of said vitamin K, about 0.1 mg to about 0.2 mg of said cyanocoalbumin, about 1.00 mg of said vitamin D3, about 100 mg to about 400 mg of said magnesium gluconate, about 30 mg to about 80 mg of said zinc sulfate heptahydrate, about 30 mg to about 100 mg of said iron sulfate heptahydrate, and about 1,000 mg to about 5,000 mg of said potassium citrate monohydrate.

6. The dietary supplement of claim 5 further comprising at least one flavoring agent in said mixture.

7. The dietary supplement of claim 6 wherein said at least one flavoring agent comprises at least one of vanilla extract liquid, French Vanilla flavor, lecithin and dextrose.

8. The dietary supplement of claim 7 wherein said at least one flavoring agent comprises about 10,000 mg of said vanilla extract liquid, about 10.00 mg of said French vanilla flavor, about 3,750 mg of said lecithin, and about 7,500 mg of said dextrose.

9. The dietary supplement of claim 5 wherein said daily dose of said mixture comprises about 45,000 mg of said whey protein, about 15,000 mg of said glutamine, about 35,000 mg of said fructose, about 15,000 mg of said maltrin, about 5,000 mg of said oat bran, about 2,500 mg of said flaxseed oil powder, about 1,500 mg of said margarine powder, about 750 mg of said isoleucine, about 1,050 mg of said leucine, about 900 mg of said lysine, about 980 mg of said methionine, about 1050 mg of said phenylalanine, about 530 mg of said threonine, about 750 mg of said valine, about 750 mg of said histidine, about 80 mg of said ascorbic acid, about 15 mg of said niacin, about 0.03 mg of said vitamin E, about 7 mg of said pantothenic acid, about 1.60 mg of said vitamin B6, about 1.60 mg of said riboflavin, about 1.20 mg of said thiamine monocitrate, about 2.99 mg of said beta carotene, about 0.33 mg of said folic acid, about 3.00 mg of said biotin, about 0.60 mg of said vitamin K, about 0.20 mg of said cyanocoalbumin, about 1.00 mg of said vitamin D3, about 300 mg of said magnesium gluconate, about 60 mg of said zinc sulfate heptahydrate, about 70 mg iron sulfate heptahydrate, and about 3,000 mg of said potassium citrate monohydrate.

10. The dietary supplement of claim 9 further comprising at least one flavoring agent in said mixture.

11. The dietary supplement of claim 10 wherein said at least one flavoring agent comprises at least one of vanilla extract liquid, French Vanilla flavor, lecithin and dextrose.

12. The dietary supplement of claim 11 wherein said at least one flavoring agent comprises about 10,000 mg of said vanilla extract liquid, about 10.00 mg of said French Vanilla flavor, about 3,750 mg of said lecithin, and about 7,500 mg of said dextrose.

* * * * *